(12) United States Patent
Green

(10) Patent No.: US 12,186,512 B2
(45) Date of Patent: Jan. 7, 2025

(54) TREATMENT FOR DRY EYES

(71) Applicant: Christopher Green, Bend, OR (US)

(72) Inventor: Christopher Green, Bend, OR (US)

(*) Notice: Subject to any disclaimer, the term of this patent is extended or adjusted under 35 U.S.C. 154(b) by 27 days.

(21) Appl. No.: 17/511,238

(22) Filed: Oct. 26, 2021

(65) Prior Publication Data

US 2022/0126077 A1    Apr. 28, 2022

Related U.S. Application Data

(60) Provisional application No. 63/105,792, filed on Oct. 26, 2020.

(51) Int. Cl.

| | | |
|---|---|---|
| *A61K 47/02* | (2006.01) | |
| *A61K 31/05* | (2006.01) | |
| *A61K 31/075* | (2006.01) | |
| *A61K 31/122* | (2006.01) | |
| *A61K 31/522* | (2006.01) | |
| *A61K 47/36* | (2006.01) | |
| *A61K 47/44* | (2017.01) | |
| *A61M 35/00* | (2006.01) | |

(52) U.S. Cl.
CPC ........... *A61M 35/003* (2013.01); *A61K 31/05* (2013.01); *A61K 31/075* (2013.01); *A61K 31/122* (2013.01); *A61K 31/522* (2013.01); *A61K 47/02* (2013.01); *A61K 47/36* (2013.01); *A61K 47/44* (2013.01)

(58) Field of Classification Search
CPC ... A61M 35/003; A61K 31/05; A61K 31/075; A61K 31/122; A61K 31/522; A61K 47/02; A61K 47/36; A61K 47/44; A61K 9/0014; A61K 9/06; A61K 9/0048; A61F 9/0008; A61P 27/02
See application file for complete search history.

(56) References Cited

U.S. PATENT DOCUMENTS

| | | | | |
|---|---|---|---|---|
| 2005/0244441 A1* | 11/2005 | Courtois | ................ | A61K 8/042 512/1 |
| 2012/0095439 A1* | 4/2012 | de Juan, Jr. | ............. | A61P 27/02 530/387.3 |
| 2013/0224293 A1* | 8/2013 | Dokou | .................... | A61P 11/00 424/464 |
| 2014/0221941 A1* | 8/2014 | Erickson | ............... | A61F 9/0017 604/294 |
| 2015/0125539 A1* | 5/2015 | Popov | .................. | A61K 9/5138 424/497 |
| 2016/0220475 A1* | 8/2016 | Scherner | ................ | A61Q 19/00 |
| 2017/0087199 A1* | 3/2017 | Patron | .................. | A61K 31/381 |
| 2018/0292403 A1* | 10/2018 | de Juan, Jr. | ............. | A61P 27/02 |
| 2019/0105283 A1* | 4/2019 | Anderson | ............... | A61L 15/44 |
| 2021/0228622 A1* | 7/2021 | Kesler | .................... | A61K 9/107 |
| 2022/0110993 A1* | 4/2022 | Lieberman | .......... | A61M 35/003 |

FOREIGN PATENT DOCUMENTS

| | | | | |
|---|---|---|---|---|
| WO | WO-2011146483 A1 * | 11/2011 | .......... | A61F 9/0017 |
| WO | WO-2017087647 A1 * | 5/2017 | ............. | A61K 31/17 |
| WO | WO-2020247594 A1 * | 12/2020 | ............... | A61K 8/64 |

* cited by examiner

*Primary Examiner* — Kai H Weng
*Assistant Examiner* — Alessandro R Del Priore
(74) *Attorney, Agent, or Firm* — Donn K. Harms

(57) ABSTRACT

A balm mixture is provided for treating dry eyes. The balm mixture is applied from a container to the skin of the user adjacent their lower eyelid. The balm mixture includes a carrier portion and an active ingredient portion which will cause tears to form in the eye of a user adjacent the application thereof, thereby alleviating a dry eye condition.

8 Claims, 2 Drawing Sheets

TREATMENT FOR DRY EYES

This application claims priority to U.S. Provisional Patent application Ser. No. 63/105792, filed on Oct. 26, 2020, which is incorporated herein in its entirety by this reference thereto.

BACKGROUND OF THE INVENTION

1. Field of the Invention

The present invention relates to a treatment for those who suffer from dry eye syndrome. More particularly, it relates to a treatment to alleviate dry eye and the eye fatigue caused thereby, which employs a balm applied to the skin adjacent the eye, rather than depositing medication actually into the eye of a patient or user.

2. Prior Art

Dry eye syndrome, also known medically as keratoconjunctivitis sicca (KCS), is a condition where the patient suffers from continually dry eyes. Because the eyelid requires fluid lubrication to easily open and close in contact with the exterior surface of the eye, dry eye syndrome is a constant irritant to those afflicted.

Additional symptoms suffered by many with dry eye syndrome include irritation, redness, eye discharge, and easily fatigued eyes. Blurred vision may also occur due to the inability of the eyelid to clean debris and particulate from the eye surface in a normal fashion. These symptoms can range from mild and occasional, for some of those afflicted, to severe and continuous for others. A particular problem for all sufferers is that scarring of the cornea may occur without some treatment or medical intervention.

As can be discerned from the name, dry eye syndrome occurs when either the eye or tear ducts communicating therewith, do not produce enough tears to sufficiently lubricate the eye surface. This problem may also be caused or exacerbated when produced tears evaporate too quickly.

It has been thought such dry eyes, from lack of tear production, can result from ongoing contact lens use, meibomian gland dysfunction, allergies, pregnancy, vitamin A deficiency, LASIK surgery, and certain medications, such as antihistamines. Also, it is known that some blood pressure medications, hormone replacement therapies, and antidepressants can cause a lack or shortage of tear production. Consequently, there are many people who suffer from such dry eyes for a wide variety of reasons.

Conventionally, treatment depends on the underlying cause of the shortage of or lack of tear production. In most cases, artificial tears are the usual first line treatment. This requires the patient to carry a bottle of tears with them and constantly place liquid drops directly into the eye. Such is a constant aggravation for those with dry eyes, and in many cases, an ongoing potential for communicating bacteria and pathogens into the eyes, caused by contaminated liquids or from the user rubbing their eyes after depositing drops therein whereby bacteria and other pathogens on the skin are communicated into the eyes.

Other options, not involving eye drop deposits to the eyes, include wrap-around eyewear that seal against or fit close to the face to decrease tear evaporation. Another treatment conventionally employed is invasive and requires the positioning of lacrimal plugs permanently into eye ducts which prevent the fluid tears from draining from the surface of the eye.

The forgoing examples of related art in the field of dry eye treatments and limitations related therewith are intended to be illustrative and not exclusive, and they do not imply any limitations on the balm treatment herein. Various limitations of the related art will become apparent to those skilled in the art upon a reading and understanding of the specification below and the accompanying drawings.

SUMMARY OF THE INVENTION

The eye balm system and dry eye relief method herein, eliminates the need for directly positioning liquids or prescription medications into the eyes and/or invasive procedures which many users find irritating, both to their eye and also the constant need to initiate treatment. Instead, the system herein, employs a specially formulated balm which is applied to the skin adjacent to but outside the eye itself. The balm, so positioned, acts to energize tear production by the eyes and constant communication of natural liquid tears to the surface of the eyes. Thus, instead of constant and repetitive deposits to the eye of a user of drops and the like, the dry eye balm treatment system herein disclosed achieves dry eye relief through the provision of a balm which is formulated to activate natural tear production, once the balm is positioned outside and adjacent the eye itself, on the skin proximate thereto.

Thus, the system and balm employed herewith, in the method herein, eliminate the need for initial and ongoing constant depositing of medications and liquids directly into the eye and the aggravation and potential for infection caused thereby.

The system herein employs a formulated balm, adapted for application to the skin of a user adjacent their eye, which is formulated to communicate with and thereafter energize the tear glands, or lacrimal glands, to produce and communicate liquid tears to the exterior surface of the eye of the user. These lacrimal glands are positioned under the upper eyelids and communicate tears through ducts, to the exterior surface of the eye. These liquid tears, in turn, wash down from the glands, especially when the eyelid blinks, and form a liquid layer over the exterior surface of the eyes. Thereafter, in a natural process, some of the liquid tears drain from the eyes through tear ducts, or lacrimal ducts.

By eliminating any deposit of user-carried medications or eye drops into the eyes and the natural user inclination to rub their eyes during and after such deposits, the potential for infection from pathogens in the liquid, itself, or on adjacent skin surfaces is eliminated. Further, since the production of tears is enhanced to communicate to the eye naturally, from the lacrimal glands to the eyes, and to drain from the lacrimal ducts, the need for duct plugs and/or eye covering eyewear to maintain a humid surrounding, is eliminated.

The balm may be formed for storage within a covered container, as a cream, or in a more particularly preferred mode, in a stick which may be extended during use from a sealable container by the user. The forming of the balm herein, as a stick, is particularly preferred in that it does not require the user to touch the balm deposited to the skin adjacent the eyes and possibly contaminate it with bacteria or pathogens their hands may have previously contacted.

The formulation particularly preferred for the balm includes caffeine, in a medically useful amount, which, when applied to the skin adjacent the eyes, promotes blood circulation thereto. Additionally included is menthol in a medically useful amount, which is included to release a vapor over a period of time subsequent to application to the skin. This vapor has been found, in testing, to stimulate the lacrimal glands to produce tears, which are communicated to the surface of the eye, though tear ducts.

It has been found in experimentation that the caffeine and menthol, when applied together to the skin adjacent the eyes, have a symbiotic relationship which enhances the production of tears by the lacrimal glands, beyond that of using menthol alone. As such the balm herein applied in the system herein to the skin adjacent the eyes, will include both menthol and caffeine to provide the most effective balm mixture. By adjacent to the eye is meant the skin area on the face which is below the lower eye lid, and between the end of the nose of the user and the outside end of the eye of the user which is closest to the ear on the same side as the eye being treated.

In addition to the mixture of menthol with caffeine, to produce the enhanced tear production, the balm includes medically acceptable additives available to those skilled in the art. These additives include binders, stabilizers, preservatives and in some cases pigments where the balm may also be employed to enhance the appearance of skin under and adjacent the eyes of the user.

With respect to the above description, before explaining at least one preferred embodiment of the herein disclosed dry eye treatment balm and method in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based, may readily be utilized as a basis for designing and configuring other balm treatments positioned on eye-adjacent skin surfaces, and for carrying out the several purposes of the present disclosed device. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements. Finally, unless provided with a specific different respective definition, the term "substantially" herein, means plus or minus five percent.

It is an object of this invention to provide a treatment for dry eye syndrome sufferers.

It is a further objection of the invention to provide such a treatment which encourages natural tear production which does not require depositing any medication or treatment directly into or onto the eye of a user.

It is an additional object of this invention to provide such a dry eye treatment and method which eliminates the need for eyewear, and the like, used to conventionally cover dry eyes and maintain a humid or moist surrounding.

These and other objects of the dry eye treatment and method herein, will be brought out in the following part of the specification, wherein detailed description is for the purpose of fully disclosing the invention without placing limitations thereon.

BRIEF DESCRIPTION OF DRAWING FIGURES

The accompanying drawings, which are incorporated herein and form a part of the specification, illustrate some, but not the only or exclusive, examples of embodiments and/or features of the invention. It is intended that the embodiments and figures disclosed herein are to be considered illustrative rather than limiting.

DETAILED DESCRIPTION OF THE PREFERRED EMBODIMENTS OF THE INVENTION

Figures 1, 2:
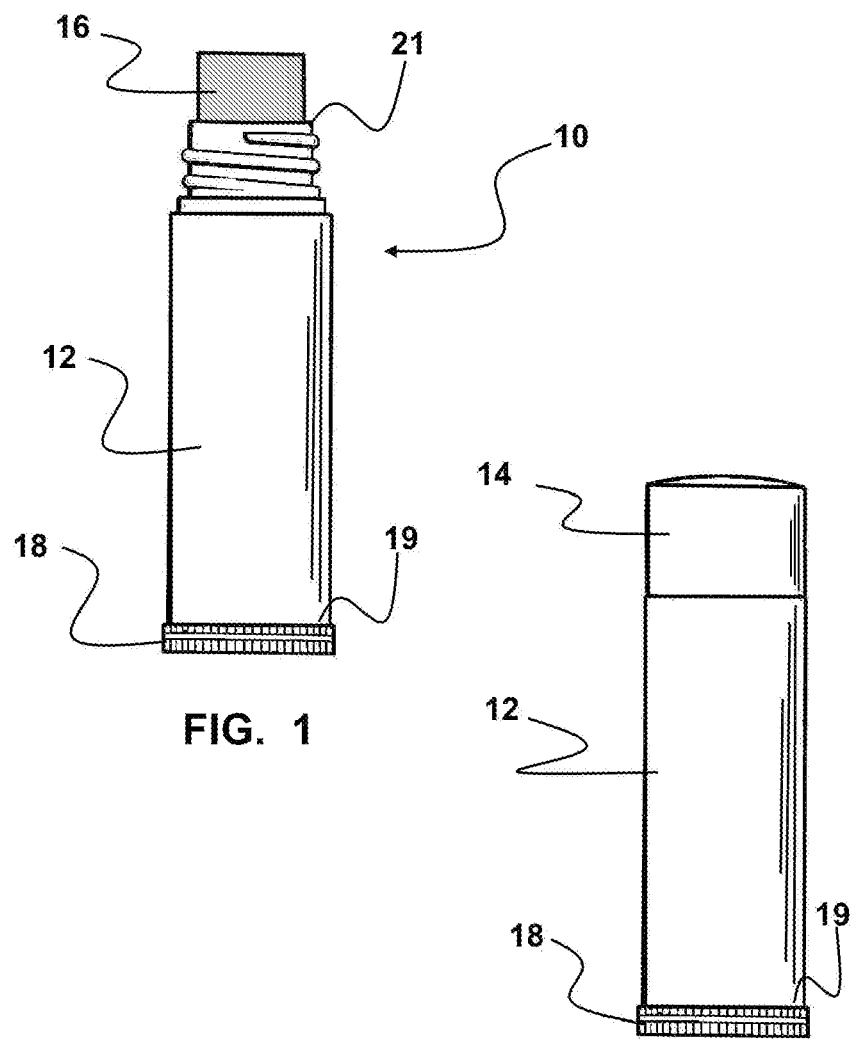
FIG. 1 shows a perspective view showing the preferred balm mixture formed to a user-deployable stick from a container, whereby it may be applied to the skin adjacent the eyes without contact with the hands or fingers.
FIG. 2 depicts the device of FIG. 1 showing a protective cap for removably covering the balm mixture, when not in use, to protect against contamination.

In this description, the directional prepositions of up, upwardly, down, downwardly, front, back, top, upper, bottom, lower, left, right and other such terms refer to the device as it is oriented and appears in the drawings and are used for convenience only. They are not intended to be limiting or to imply that the device has to be used or positioned in any particular orientation.

Now referring to drawings in FIGS. 1-4, wherein similar components are identified by like reference numerals, there is seen in FIG. 1 the balm formulation herein, which is distributed in a container 12. It should be noted that the container could also be a jar with a cap, wherein the user will use their fingers to apply the balm. However, experimentation has shown that a much more evenly distributed amount of balm in the area adjacent the lower eye lid is applied where the container 12 surrounds the balm mixture 16 which is dispensed by projecting a portion from the open end of the container 12 using the dispensing component 18, which in the preferred modes herein in FIG. 1-3, employs a rotating knob 19 which actuates a screw mechanism or the like engaged with the balm 16, formed as a stick.

In all modes herein, the container 12 has a removable cap 14 which serves to seal the container 12 from the outside atmosphere and prevent evaporation and hardening of the balm mixture 16 stored within an interior cavity of the container 12.

The dispensing component 18 is operatively engaged with the container 12, at a second end, which is opposite the opening at the first end or dispensing end 21 of the container 12 from which the balm 16 will dispense. A twisting of the knob 19 of the dispensing component 18 will rotate an axial or screw type projection engaged to the dispensing component 18 and extending through an engagement with the center of the balm 16. Twisting the knob 19 of the dispensing component 18 in one direction will translate the balm 16 from the dispensing end 21 of the container 12.

The balm 16 is formed of a total mixture which includes active ingredients and which includes carriers and stabilizers adapted to form the balm 16 into a stick form. In this preferred mode, the balm 16 can, thus, be dispensed from the dispensing end 21 of the container 12 by the rotation of the knob 19 of the dispensing component 18. This twist and dispense configuration renders the device 10 very convenient to employ by a user in the method herein.

Figures 3, 4:
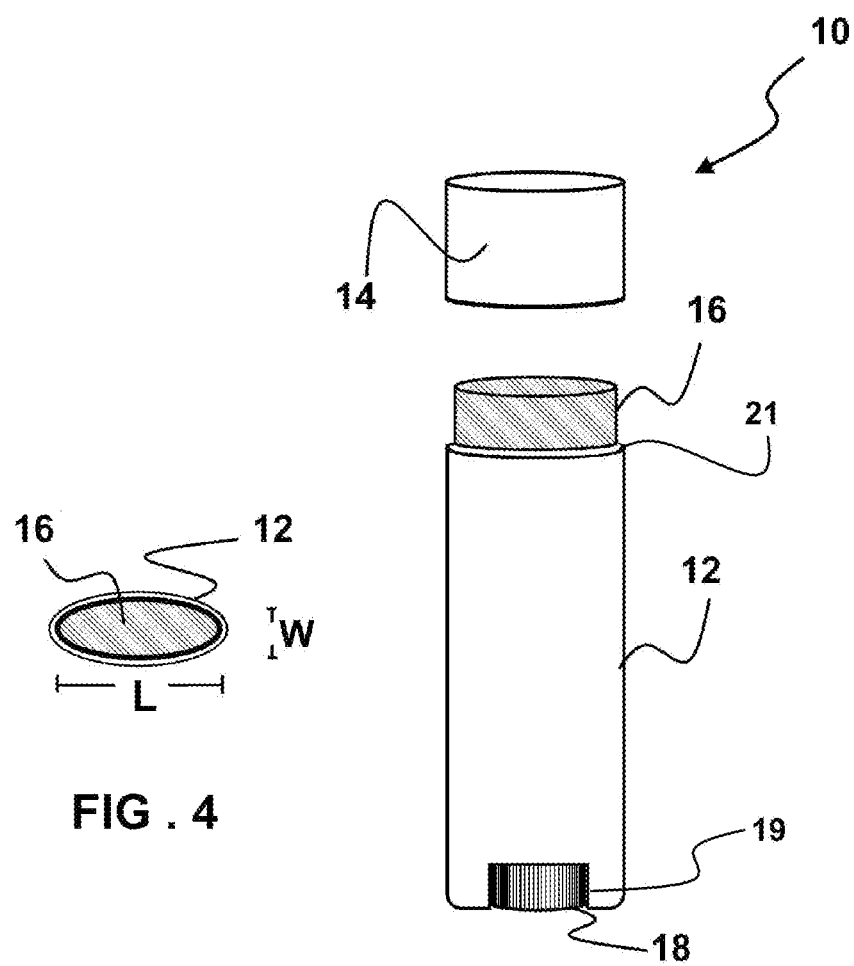
FIG. 3 depicts an especially preferred shape of the dispensing container and the balm mixture dispensed therefrom which has been found to render it easier for users to apply.
FIG. 4 is an end view of the preferred container of FIG. 3 showing a preferred length and width of the dispensed balm.

FIGS. 3-4 depict an especially preferred shape and dimensional size of the dispensing container and the balm 16 mixture dispensed therefrom. This oval shape and the length and width, thereof, have been found to render the device 10 easier for users to apply. As shown, the container 12 is shaped to surround and support the balm mixture 16 in a member or stick form, which has a length L of substantially 0.70 to 1.0 inches and a width W, of substantially 0.4 to 0.6 inches. It was found in experimentation that this oval shape, in the dimensions noted, of the balm mixture formed in a stick or member, allowed the user to deposit the balm 16 onto the skin adjacent the lower lid of their eye easier and in one swipe, rather than in multiple swipes. The oval shape of the container 12 also was found to render it easier to hold and more securely held during application of the balm 16 adjacent the lower lid of the eye of the user, which helped prevent the accidental contact of the balm 16 with the eyeball of the user during application.

The total volume of the balm mixture includes a carrier mixture portion thereof, blended with an active ingredient mixture portion of the balm mixture. The active ingredient mixture portion includes a plurality of active ingredients.

Currently, the carrier portion of the total volume of the balm mixture, forms between 40 to 80 percent of the total volume of the balm mixture.

Currently, the carrier mixture portion preferably includes an oil portion thereof, where the oil portion includes at least one oil, and preferably a combination of oils, from a group of oils including: *Ricinus communis* (Castor) Seed Oil, *Butyrospermum parkii* (Shea) Butter, Petrolatum, Octyldodecanol, Mineral Oil (Paraffinum Liquidum), *Simmondsia chinensis* (Jojoba) Seed Oil and Lanolin.

Included with the carrier mixture portion with the oil portion thereof, is a wax portion of the carrier mixture. The wax portion of the carrier mixture portion includes one or a combination of waxes, from a group of waxes, including: Beeswax (Cera Alba), a hard and higher melting point wax, *Euphorbia cerifera* (Candelilla Wax), and a high melting point, brittle wax, such as Carnauba Wax (*Copernicia cerifera* Cera).

Also included in the carrier mixture portion is a film forming additive or powder such as talc or in the current preferred mode, corn starch.

Currently, the carrier mixture portion includes a mixture of castor seed oil, carnauba wax, and corn starch. However, one or more oils, from the noted group of oils, can be substituted or included with the castor seed oil, and one or more waxes, from the group of waxes noted above, can be included with or substituted for the carnauba wax. While corn starch is preferred, a film forming particulate ingredient or additive, talc or other cosmetic powders may be substituted.

The plurality of active ingredients have been found, in experimentation when employed together, to have a beneficial synergistic effect which is well beyond the effect of the individual ingredients when employed in a balm by themselves. Currently, an active ingredient portion of the total volume of the balm mixture, includes a combination of active ingredients blended and combined to an active ingredient portion of the total balm mixture. This active ingredient portion of the total mixture ranges from 20 to 60 percent of the total volume of the balm mixture.

Included in the active ingredient portion of the balm mixture, to achieve the synergistic effect noted to cause enhanced moisture generation in the eyes, are Menthoxypropanediol, Menthanediol, Menthol, and Caffeine. Currently, the percentage of the synergistic active ingredients, in the active ingredient portion, of the total volume of the balm mixture to be blended with the carrier mixture portion, are:

Menthoxypropanediol=30-40% of the active ingredient portion,
with 36.35% being a current favored amount.
Menthanediol=30-40% of the active ingredient portion,
with 36.36% being a current favored amount.
Menthol=20-30% of the active ingredient portion,
with 27.27% being a currently favored amount;
and Caffeine=0.01-0.025% of the active ingredient portion,
with 0.018% being a currently favored amount.

As noted, in experimentation, a synergistic effect of the combined active ingredients in the active ingredient portion, was apparent when mixed in the above noted respective favored amounts of the active ingredient portion of the total balm mixture. However, such may vary slightly, as noted above, and a similar synergistic effect is anticipated. However, currently, the above noted, currently favored respective individual amounts, are currently preferred.

In a method of treating dry eyes using a balm, a volume of balm is provided from which the user will treat their dry eyes. Using the provided balm mixture, the user will apply the balm to the skin on their face adjacent to the lower eye lid of one or both eyes. Thereafter the tears in the eye of the user will be increased upon communication of evaporating vapors from the balm mixture applied to the skin adjacent their lower eyelid.

While all of the fundamental characteristics and features of the eye balm for treatment of dry eyes and system of employment thereof have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are considered included within the scope of the invention as defined by the following claims.

What is claimed is:

1. A balm mixture for application to a skin of a user adjacent a lower eyelid thereof, said balm mixture comprising:
a carrier mixture portion and an active ingredient portion;

said carrier mixture portion being 40 to 80 percent of the total volume of the balm mixture;

said active ingredient portion being 20 to 60 percent of the total volume of the balm mixture and being formed from a mixture consisting of Menthoxypropanediol, Menthanediol, Menthol, and Caffeine;

said carrier portion including a powder from a group of powders including talc and cornstarch;

said carrier mixture portion includes an oil portion thereof, where the oil portion includes at least one oil from a group of oils including: *Ricinus communis* (Castor) Seed Oil, *Butyrospernum parkii* (Shea) Butter, Petrolatum, Octyldodecanol, Mineral Oil (Parrafinum Liquidum), *Simmondsia chinensis* (Jojoba) Seed Oil and Lanolin; and said carrier mixture portion including a wax portion thereof, where the wax portion includes one or a combination of waxes, from a group of waxes including: Beeswax, Candelilla Wax, and Carnauba Wax.

2. The balm mixture of claim 1 additionally comprising:
said carrier mixture portion formed from a mixture of castor seed oil, corn starch and carnauba wax.

3. The balm mixture of claim 2 said active ingredient portion consisting of:
30-40% Menthoxypropanediol;
30-40% Menthanediol;
30-40% Menthol; and
0.01%-0.25% Caffeine.

4. The balm mixture of claim 2 said active ingredient portion consisting of:
36.35% Menthoxypropanediol;
36.36% Menthanediol;
27.27% Menthol; and
0.018% Caffeine.

5. The balm mixture of claim 3,
wherein said balm mixture is formed to an oval shape member for application of said balm mixture to the skin of said user.

6. A method of treating dry eyes comprising the steps of:
applying the balm mixture of claim 1 to the skin adjacent the lower eyelid.

7. A balm mixture in the form of a stick for application to a skin of a user adjacent a lower eyelid thereof, said balm mixture comprising:
a carrier mixture portion and an active ingredient portion;
said carrier mixture portion being 40 to 80 percent of the total volume of the balm mixture;
said active ingredient portion being 20 to 60 percent of the total volume of the balm mixture and being formed from a mixture consisting of:
30-40% Menthoxypropanediol;
30-40% Menthanediol;
30-40% Menthol; and
0.01%-0.25% Caffeine;
said carrier portion including a powder from a group of powders including talc and cornstarch;
said carrier mixture portion includes an oil portion thereof, where the oil portion includes at least one oil from a group of oils including: *Ricinus communis* (Castor) Seed Oil, *Butyrospernum parkii* (Shea) Butter, Petrolatum, Octyldodecanol, Mineral Oil (Parrafinum Liquidum), *Simmondsia chinensis* (Jojoba) Seed Oil and Lanolin; and
said carrier mixture portion including a wax portion thereof, where the wax portion includes one or a combination of waxes, from a group of waxes including: Beeswax, Candelilla Wax, and Carnauba Wax.

8. A balm mixture for application to a skin of a user adjacent a lower eyelid thereof, said balm mixture comprising:
a carrier mixture portion and an active ingredient portion;
said carrier mixture portion being 40 to 80 percent of the total volume of the balm mixture;
said active ingredient portion being 20 to 60 percent of the total volume of the balm mixture and being formed from a mixture consisting of:
36.35% Menthoxypropanediol;
36.36% Menthanediol;
27.27% Menthol; and
0.018% Caffeine;
said carrier portion including a powder from a group of powders including talc and cornstarch;
said carrier mixture portion includes an oil portion thereof, where the oil portion includes at least one oil from a group of oils including: *Ricinus communis* (Castor) Seed Oil, *Butyrospernum parkii* (Shea) Butter, Petrolatum, Octyldodecanol, Mineral Oil (Parrafinum Liquidum), *Simmondsia chinensis* (Jojoba) Seed Oil and Lanolin; and
said carrier mixture portion including a wax portion thereof, where the wax portion includes one or a combination of waxes, from a group of waxes including: Beeswax, Candelilla Wax, and Carnauba Wax.

\* \* \* \* \*